(12) United States Patent
Melsheimer

(10) Patent No.: US 7,578,838 B2
(45) Date of Patent: Aug. 25, 2009

(54) DELIVERY SYSTEM WITH HELICAL SHAFT

(75) Inventor: Jeffry S. Melsheimer, Springville, IN (US)

(73) Assignee: Cook Incorporated, Bloomington, IN (US)

( * ) Notice: Subject to any disclaimer, the term of this patent is extended or adjusted under 35 U.S.C. 154(b) by 303 days.

(21) Appl. No.: 11/034,913

(22) Filed: Jan. 12, 2005

(65) Prior Publication Data

US 2006/0155357 A1    Jul. 13, 2006

(51) Int. Cl.
*A61F 2/84* (2006.01)
(52) U.S. Cl. ..................... 623/1.11; 623/1.23
(58) Field of Classification Search ............... 623/1.11, 623/1.23, 1.2, 1.34, 1.16, 1.12; 606/108
See application file for complete search history.

(56) References Cited

U.S. PATENT DOCUMENTS

| | | | | |
|---|---|---|---|---|
| 4,768,507 A | * | 9/1988 | Fischell et al. | 623/1.11 |
| 4,960,410 A | * | 10/1990 | Pinchuk | 604/96.01 |
| 5,797,952 A | * | 8/1998 | Klein | 623/1.12 |
| 5,807,398 A | * | 9/1998 | Shaknovich | 623/1.11 |
| 5,843,050 A | * | 12/1998 | Jones et al. | 604/525 |
| 6,083,237 A | * | 7/2000 | Huitema et al. | 606/180 |
| 6,334,871 B1 | * | 1/2002 | Dor et al. | 623/1.34 |
| 2002/0038141 A1 | * | 3/2002 | Yang et al. | 623/1.12 |
| 2002/0151952 A1 | * | 10/2002 | Perouse | 623/1.11 |
| 2003/0023298 A1 | * | 1/2003 | Jervis | 623/1.11 |

* cited by examiner

*Primary Examiner*—Anhtuan T. Nguyen
*Assistant Examiner*—Ryan J Severson
(74) *Attorney, Agent, or Firm*—Brinks Hofer Gilson & Lione

(57) ABSTRACT

A delivery system is provided for releasing a medical device within a body cavity. The delivery system may be used in an intravascular procedure to implant a self-expandable stent. A helical structure on the shaft of the delivery system engages the inner surface of the stent. As a result, the stent may be released by rotating the shaft relative to the stent which pushes the stent forward from the distal end of the shaft.

30 Claims, 2 Drawing Sheets

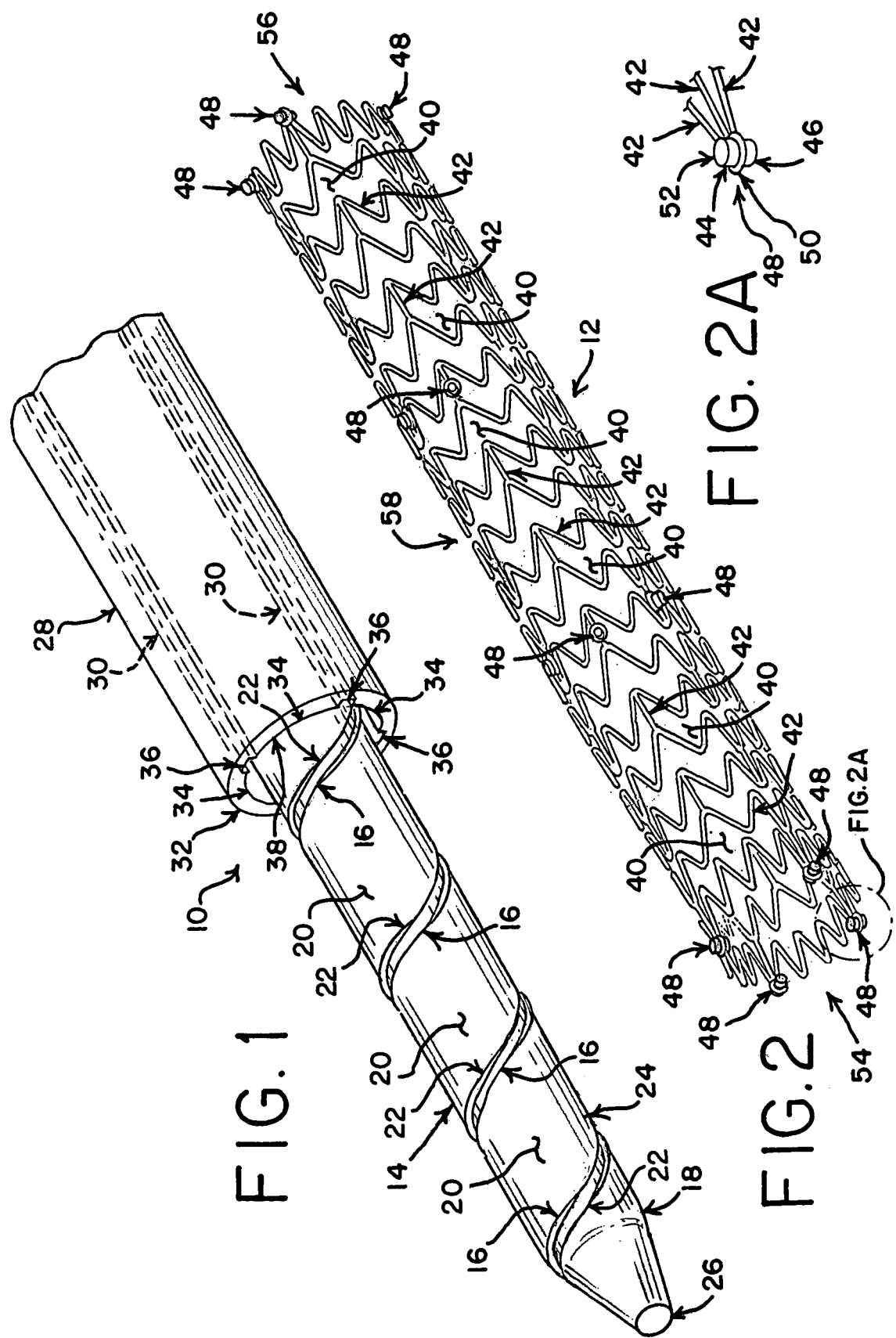

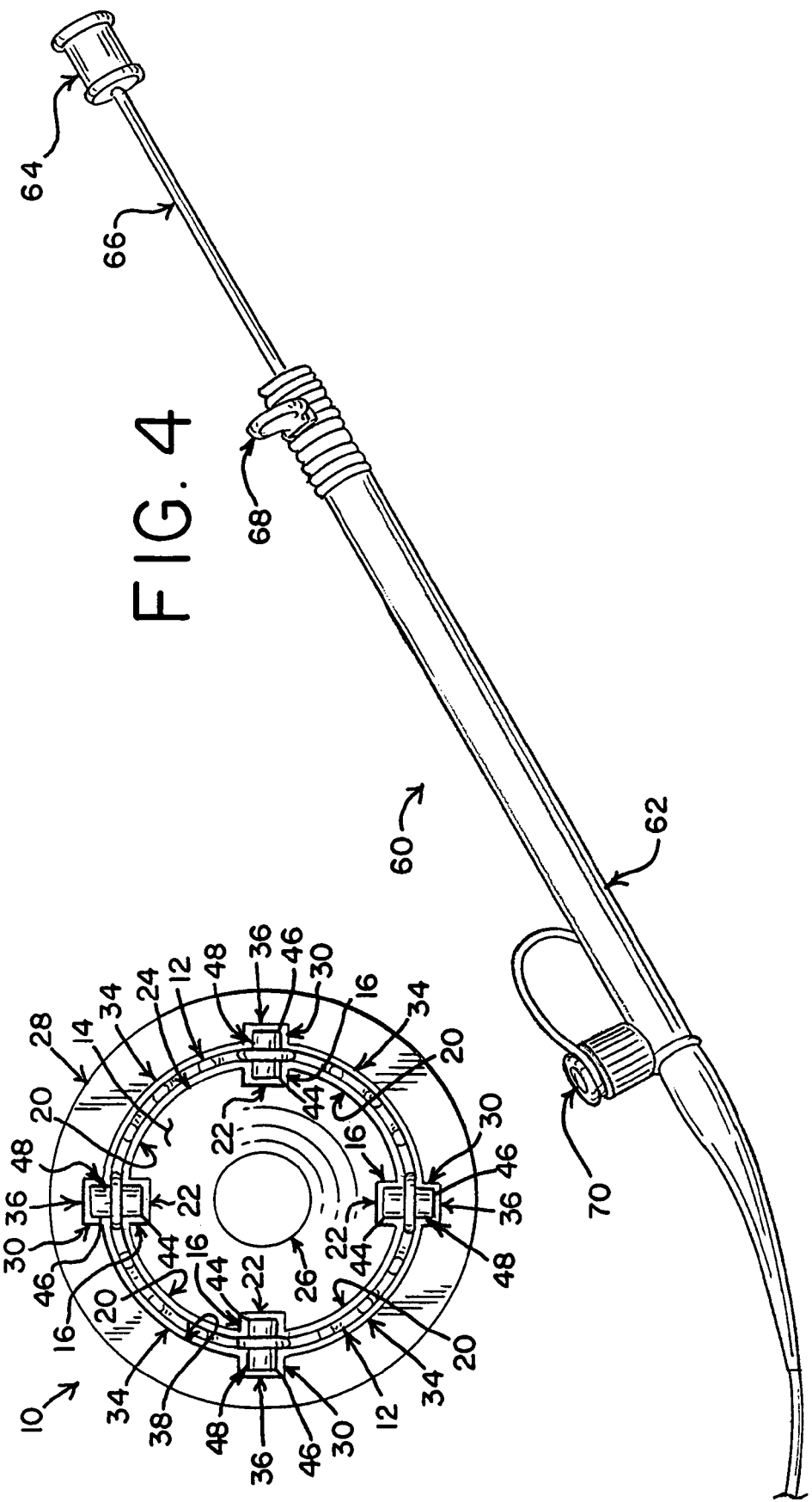

DELIVERY SYSTEM WITH HELICAL SHAFT

BACKGROUND

The present invention relates generally to medical devices and more particularly to a delivery system in which the medical device is interposed between a shaft and a sheath.

The use of stents to treat various organs, such as the vascular system, colon, biliary tract, urinary tract, esophagus, trachea and the like, has become common in recent years. Stents are useful in a variety of medical procedures and are often used to treat blockages, occlusions, narrowing ailments and other related problems that restrict flow through a passageway. One common medical procedure in which stents are used involves implanting an endovascular stent into the vascular system. Stents have been shown to be useful in treating numerous vessels throughout the vascular system, including coronary arteries, peripheral arteries (e.g., carotid, brachial, renal, iliac and femoral), and other vessels.

Although stents and other medical devices are used in many different procedures, the use of stents in coronary arteries has drawn particular attention from the medical community because of the growing number of people suffering from heart problems associated with stenosis (i.e., narrowing of the arterial lumen). This has lead to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Stents have become a popular alternative for treating coronary stenosis because stenting procedures are considerably less invasive than other alternatives. Traditionally, stenosis of the coronary arteries has been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient. To address the growing demand for non-invasive medical procedures for treating coronary arteries and other passageway problems, the medical community has begun to turn away from conventional invasive procedures like bypass surgery and increasingly the treatment of choice now involves various types of stenting procedures.

Many different types of stents and stenting procedures are possible. In general, however, stents are typically designed as tubular support structures that may be inserted percutaneously and transluminally through a body passageway. Traditionally, stents are made from a metal or other synthetic material with a series of radial openings extending through the support structure of the stent to facilitate compression and expansion of the stent. Although stents may be made from many types of materials, including non-metallic materials, common examples of metallic materials that may be used to make stents include stainless steel, nitinol, cobalt-chrome alloys, amorphous metals, tantalum, platinum, gold and titanium. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through various narrow body passageways to the area to be treated while the stent is in a relatively small, compressed diameter. Once the stent has been positioned and expanded at the area to be treated, the tubular support structure of the stent contacts and radially supports the inner wall of the passageway. As a result, the implanted stent mechanically prevents the passageway from closing and keeps the passageway open to facilitate fluid flow through the passageway.

Particular stent designs and implantation procedures vary widely. For example, stents are often generally characterized as ether balloon-expandable or self-expandable. However, the uses for balloon-expandable and self-expandable stents frequently overlap and procedures related to one type of stent are frequently adapted to other types of stents.

Self-expandable stents are increasingly being used by physicians because of their adaptability to different conditions and procedures. Self-expandable stents are usually made of shape memory materials or materials that act like a spring. Typical metals used in this type of stent include nitinol and 304 stainless steel. A common procedure for implanting a self-expandable stent involves a two-step process. First, the narrowed vessel portion to be treated is dilated with an angioplasty balloon. Second, the stent is implanted into the dilated vessel portion. However, other procedures are also possible, such as adding an additional dilation step after stent implantation or implanting a stent without dilation. To facilitate stent implantation, the stent is installed on the end of a catheter in a small, compressed state. The stent is usually retained in the compressed state by inserting the stent into a sheath at the end of the catheter. The stent is then guided to the portion of the vessel to be treated as described above. Once the catheter and stent are positioned adjacent the portion to be treated, the stent is released by pulling, or withdrawing, the sheath rearward. Normally, a step or other feature is provided on the catheter to prevent the stent from moving rearward with the sheath. After the stent is released from the retaining sheath, the stent radially springs outward to an expanded diameter until the stent contacts and presses against the vessel wall. Traditionally, self-expandable stents have been used in a number of peripheral arteries in the vascular system due to the shape memory characteristic of these stents. One advantage of self-expandable stents for peripheral arteries is that traumas from external sources do not permanently deform the stent. Instead, the stent may temporarily deform during an unusually harsh trauma but will spring back to its expanded state once the trauma is relieved. However, self-expandable stents may be used in many other applications as well.

The above-described examples are only some of the applications in which intravascular devices are used by physicians. Many other applications for intravascular devices are known and/or will be developed in the future. For example, similar intravascular procedures are also used to implant stent-grafts to treat aneurysms, to deploy vascular filters, and to implant artificial valves in veins.

Typically, intravascular devices are provided with markers and/or pushing members that are attached or formed along the proximal and/or distal ends of the device structure. These features may be used for a number of purposes and often serve more than one function. For example, markers are usually provided at both the proximal and distal ends of the intravascular device to assist the physician in positioning the device during intravascular procedures. Generally, separate markers are needed on most intravascular devices since the structure of the device itself usually cannot be seen easily on x-ray or other visualization equipment. This is due in part to the types of material that are usually used in intravascular devices and the slenderness of the structural members often used in the structure of the device. Markers address this visualization problem by providing features with increased radiopacity along the proximal and distal ends of the device. Typically, the markers are usually filled with a radiopaque material like gold or platinum. As a result, the radiopaque material in the markers can be seen more easily on the physician's visualization equipment than the structure of the device itself.

Pushing members are also used at the proximal and/or distal ends of many intravascular devices. In general, the pushing members provide a contact surface that allows the device to be moved by pushing against the pushing members. Pushing members may be used at several different stages. For example, during the manufacture of expandable devices and the corresponding delivery systems, the intravascular device is usually loaded into the delivery system in a compressed state. Many different types of delivery systems for intravascular devices are known to those in the art, and therefore a detailed description is unnecessary. However, as described above, delivery systems often include a retaining sheath at the end of a catheter that restrains the outer surface of the device and keeps the device compressed until the intravascular device is released within the patient's body. A common manufacturing method for loading intravascular devices into the retaining sheath involves compressing the device while at the same time pushing on one end of the device in order to slide the device into the sheath. Alternatively, the device may be compressed and pushed into a transfer tube first and then pushed again through the transfer tube into the delivery system.

Pushing members are also used on the proximal end of intravascular devices in order to release the device from the delivery system. As previously described, intravascular devices may be released by pulling the retaining sheath off the device. Typically, the delivery system also includes a step or other structure within the retaining sheath which contacts the proximal end of the device. Generally, the step and the sheath are designed to move relative to each other so that as the sheath is pulled back, the step is maintained in place. As a result, the step prevents the device from moving rearward with the retaining sheath as the sheath is pulled back. In effect, the device is pushed forward relative to the sheath which is pulled rearward.

Typically, the markers on an intravascular device are also used as pushing members and vice versa. Normally, the markers are used as pushing members by pushing on the end surface of the markers. However, at least in the case of stents, current markers may be inadequate when used as pushing members. This can be a particular problem on longer length stents. Generally, most stents that are currently used for medical treatments are 8 cm or less in length. However, stents that are longer than 8 cm are becoming more desirable to treat various peripheral arteries, such as the superficial femoral artery. When longer stents like these are pushed, either during loading into the delivery system or during release, higher frictional forces must be overcome in order to move the stent. The longer length of some of these stents also makes the stent generally less stable than shorter stents. As a result, buckling and deformation problems that may occur when pushing on a stent tend to be more pronounced and damaging on longer stents. However, these types of problems may exist with any stent.

One problem with current delivery systems for intravascular devices is that it can be difficult to precisely release the device within a body cavity. For example, in the case of a body lumen, such as an artery, it is often important to precisely position the intravascular device longitudinally within the artery. One particular example where physicians may be concerned about this issue is the placement of a stent within an artery to treat a stenosed area. Typically, the length and diameter of the stent is chosen by the physician based on the particular artery being treated and the area of stenosis. However, on occasion the physician may encounter difficulties during the intravascular procedure which results in the stent being implanted at a less than optimal location. For example, the stent may be released either longitudinally distal or proximal to the desired placement. As a result, the stenosed area may not be completely covered by the stent. If this occurs, the physician may need to perform a second procedure to implant a second stent to cover the remaining untreated stenosed area. This results in greater costs and increased risks due to the extra procedures involved. In addition, the desirable restenosis of the artery wall that usually encapsulates the stent after implantation may not fully encapsulate the overlapped portion of the stents. Moreover, when metal stents are used, the overlapping contact between the two stents may corrode and cause an allergic reaction in the patient.

Precise positioning of intravascular devices can be important in a variety of other procedures and for other reasons as well. For example, it can also be important to precisely position stents or other intravascular devices when the device is being released near an artery bifurcation or near another organ or structure. Procedures related to treating aneurysms also may require precise positioning of a device. Precise positioning of an intravascular device may be made more difficult for a number of reasons. One problem that physicians have encountered is a tendency of self-expandable stents and similar devices to "jump" out of the delivery device during release. This may occur when the distal end of the stent is initially released and the proximal end of the stent is still within the delivery system. Since self-expandable stents are elastic and seek an expanded diameter, the distal end of the stent may rapidly expand in this situation and unexpectedly pull the proximal end of the stent out of the delivery system. This can make positioning of the stent difficult to control. The control mechanism may also make precise positioning difficult. Normally, in the case of self-expandable stents, the control mechanism includes a first handle attached to the sheath and a second handle attached to a core and/or step. Typically, the physician releases the stent by holding the second handle in a fixed position while pulling the first handle rearward. This causes the sheath to move rearward relative to the core and/or step. The step prevents the stent from moving rearward with the sheath, and as a result, the stent is released by the withdrawal of the sheath. However, the physician may find it difficult to precisely control the movement between the two handles, which may cause the stent or other device to be released in a less than optimal position.

Another problem with conventional delivery systems is that they are usually not adapted to implant more than one intravascular device at a time. However, in many procedures multiple devices may need to be released within the body cavity being treated. As a result, the physician may need to introduce and withdraw several different delivery systems through the patient's passageways to complete the procedure. The disadvantage of this is that each time a delivery system must be introduced and withdrawn damage may occur to the passageways. The overall length of the procedure and the cost of the procedure is also increased.

Accordingly, it is apparent to the inventor that an improved delivery system for medical devices is needed. A solution to these and other problems is described more fully below.

BRIEF SUMMARY

A delivery system for medical devices is described which releases a medical device by turning a shaft that engages an inner surface of the medical device. In one embodiment of the delivery system, a self-expandable stent is collapsed between a shaft and a sheath. The shaft is provided with a helical groove, and the sheath is provided with longitudinal grooves. The stent is also provided with raised portions on the outer surface of the stent and raised portions on the inner surface of the stent. The outer surface raised portions engage the longitudinal grooves, and the inner surface raised portions engage the helical grooves. Additional details are described below.

BRIEF DESCRIPTION OF SEVERAL VIEWS OF THE DRAWINGS

The invention may be more fully understood by reading the following description in conjunction with the drawings, in which:

FIG. 1 is a perspective view of a delivery system for medical devices;

FIG. 2 is a perspective view of a stent which may be loaded into the delivery system;

FIG. 2A is a close-up perspective view of a marker as shown in FIG. 2;

FIG. 3 is a elevational end view of the delivery system with the stent loaded into the delivery system; and FIG. 4 is a perspective view of a control mechanism that may be used to release the stent from the delivery system.

DETAILED DESCRIPTION

Referring now to the drawings, a delivery system 10 for medical devices is shown. In particular, the embodiment shown and described is adapted for intravascular delivery of a self-expandable stent 12. However, the structure taught herein may also be adapted for other uses as well.

As shown in FIG. 1, the delivery system 10 includes a shaft 14, or core, with a helical groove 16 along a portion of the distal end 18 of the shaft 14. The helical groove 16 is defined by a helical raised region 20 and a helical recessed region 22. Thus, the interposition of the helical raised region 20 and the helical recessed region 22 forms a helical groove 16. The helical raised region 20 may form the outer circumference 24 of the shaft 14. A guidewire lumen 26 is provided through the shaft 14 to allow a guidewire to pass axially through the delivery system 10. The delivery system 10 also includes a sheath 28 that surrounds the shaft 14 and may be moved longitudinally relative to the shaft 14. The sheath 28 includes longitudinal grooves 30 extending along a portion of the distal end 32 of the sheath 28. The longitudinal grooves 30 are defined by longitudinal raised regions 34 and longitudinal recessed regions 36 which are interposed therebetween. The inner circumference 38 of the sheath 28 may be formed by the longitudinal raised region 34. Because the outer circumference 24 of the shaft 14 is smaller than the inner circumference 38 of the sheath 28, the shaft 14 and the sheath 28 may be moved longitudinally relative to each other when the shaft 14 is positioned within the sheath 28. Although the helical raised and recessed regions 20, 22 of the shaft 14 and the longitudinal raised and recessed regions 34, 36 of the sheath 28 are described here generally as grooves 16, 30 these features may also be embodied by other shapes, sizes and structures. For example, the groove 16 of the shaft 14 and/or the grooves 30 of the sheath 28 could also be embodied by fins or threads instead. In addition, the helical groove 16 could be formed by a single helical structure as shown or could be formed of multiple helical structures, e.g., like a double lead screw thread.

As shown in FIGS. 2 and 2A, one type of medical device that may be used with the delivery system 10 is a self-expandable stent 12. The stent 12 is formed as a cylindrical structure with radial holes 40 extending through the structure to allow the stent 12 to be compressed and to radially expand. Typically, the stent structure is formed by interconnected stents 42. However, many other types of stent structures are also known in the art. Positioned at various locations along the length of the stent 12 are engagement portions 44, 46 that protrude out from the outer diameter of the stent structure and in from the inner diameter of the stent structure. Preferably, the engagement portions 44, 46 are integrated with the markers 48 so that the markers 48 serve the dual purposes of allowing the physician to see the stent 12 during implantation and providing a surface to engage and move the stent 12. Thus, as shown, each of the markers 48 may be made from a ring 50 of the same material that forms the stent structure. The center region 52 of each ring 50 is filled with a radiopaque material, such as gold or platinum, so that a first raised portion 44 of the center region 52 extends inward from the stent structure and a second raised portion 46 extends outward from the stent structure. Preferably, the engagement portions 44, 46 are provided at both the distal end 54 of the stent 12 and the proximal end 56 of the stent 12. In addition, the engagement portions 44, 46 may also be provided at intermediate locations 58 along the length of the stent 12. Although the engagement portions 44, 46 of the markers 48 are described here generally as protrusions that extend out from the outer diameter of the stent structure and in from the inner diameter of the stent structure, the engagement portions may also be embodied by other shapes, sizes and structures, and the sheath and/or shaft may engage other outer or inner surfaces of a medical device. For example, the engagement portions may also be embodied by recessed features or threads. In addition, the inner diameter engagement portions may be different than the outer diameter engagement portions, e.g., longitudinal lugs on the outer diameter, and diagonal lugs on the inner diameter.

As shown in FIG. 3, the stent 12 is received between the shaft 14 and the sheath 28 with the stent 12 being collapsed into a small diameter. The sheath 28 surrounds the stent 12 and the shaft 14 and retains the stent 12 in the collapsed diameter until the sheath 28 is withdrawn. Thus, the shaft 14 engages the inner diameter of the stent, and the sheath 28 engages the outer diameter of the stent 12. As shown, the first raised portions 44 of the stent 12 are engaged by the helical groove 16 of the shaft 14, and the second raised portion 46 of the stent 12 are engaged by the longitudinal grooves 30 of the sheath 28.

Several different control mechanisms may be used with the stent delivery system 10. One preferred control mechanism 60 is shown in FIG. 4. The control mechanism 60 has a first handle 62 and a second handle 64. Typically, the first handle 62 is connected to the sheath 28, and the second handle 64 is connected to the shaft 14 through a rod 66 that passes through the first handle 62. Thus, when the first and second handles 62, 64 are moved relative to each other, the sheath 28 and the shaft 14 move correspondingly relative to each other. Optionally, a removable stopper 68 may be provided to lock the first and second handles 62, 64 to restrict relative movement between the handles 62, 64. Preferably, the stopper 68 locks both longitudinal and rotational movement. A port 70 may also be provided on the first handle 62 to pass various fluids through, or flush air from, the delivery system 10.

The operation of the delivery system 10 is now apparent. In general, the delivery system 10 may be used in at least two different manners. For example, the delivery system 10 may be used in a conventional manner by withdrawing the sheath 28 rearward from the shaft 14 and the stent 12. When used in this manner, the physician releases the stent 12 by pulling rearward on the first handle 62 attached to the sheath 28 while restraining the position of the second handle 64 attached to the shaft 14. In this technique, the physician may operate the delivery system 10 without turning either the first handle 62 or the second handle 64. Thus, the only relative movement between the first and second handles 62, 64 may be longitudinal. As a result of controlling the handles 62, 64 in this way, the sheath 28 moves rearward with the first handle 62, while the shaft 14 does not move longitudinally. Because the first raised portion 44 of the markers 48 is engaged with the helical groove 16 of the shaft 14, the stent 12 is prevented from moving rearward with the sheath 28. Thus, the rearward movement of the sheath 28 releases the stent 12, thereby allowing the stent 12 to expand to contact the artery wall.

The delivery system 10 may also be used in a rotational manner to provide more precise control over the release of the stent 12. When used in this manner, the physician turns the second handle 64 attached to the shaft 14 relative to the first handle 62 attached to the sheath 28. In this technique, the physician may operate the delivery system 10 to release the stent 12 while maintaining the longitudinal relationship of the first and second handles 62, 64 relative to each other. However, the first and second handles 62, 64 may need to be withdrawn together as the handles 62, 64 are rotated. As the shaft 14 is rotated, the engagement between the second raised portion 46 of the markers 48 with the longitudinal grooves 30 of the sheath 28 prevents the stent 12 from rotating. As a result, the engagement between the first raised portion 44 of the markers 48 and the helical grooves 16 of the shaft 14 forces the stent 12 to move relative to the sheath 28. The degree of movement of the stent 12 may be changed as desired by altering the pitch and direction of the helical groove 16 on the shaft 14. This provides the physician with greater control over the release of the stent 12 since the physician may precisely release the stent 12 in small increments by turning the second handle 64 instead of adjusting the longitudinal relationship between the first and second handles 62, 64.

The delivery system 10 also provides the physician with more flexibility since the conventional and the rotational manners described above may be used together in the same procedure. For example, the physician may choose to release the stent 12 in a conventional manner during part of the release and may choose to use the rotational manner for another part of the release. The ability to control the delivery system 10 with both a conventional manner and a rotational manner may provide other benefits as well. For example, the stent 12 may be released in alternating stages of conventional release and rotational release. In particular, a portion of the stent 12 could be released conventionally by pulling the sheath 28 rearward to expose part of the stent 12 and the shaft 14. The shaft 14 could then be rotated in reverse to withdraw the shaft 14 while leaving the exposed part of the stent 12 extending from the sheath 28 and the shaft 14. Thus, in this approach, the stent 12 may be conventionally released while also minimizing the length of the shaft 14 that extends from the sheath 28. Still other techniques for releasing a stent or other medical device may be possible.

Another advantage of the delivery system 10 is that it may minimize the jumping effect of the stent 12 when released which is sometimes experienced with conventional delivery systems. This may be achieved because the stent 12 is restricted from longitudinal movement at several places along the length of the stent 12 by the engagement between the first raised portion 44 of the markers 48 and the helical groove 16 of the shaft 14. Therefore, even when the distal end 54 of the stent 12 is released and begins to expand, the stent 12 remains longitudinally restrained by the markers 48 and the portion of the helical groove 16 that is still encompassed by the sheath 28. This advantage further improves controllability of the release of the stent 12.

Another advantage of the delivery system 10 is that the pushing force exerted on the stent 12 during stent release may be distributed more evenly across the length of the stent 12. For example, with the stent 12 shown in FIG. 2, the pushing force is shared by the markers 48 at the distal end 54, the markers 48 at the proximal end 56, the markers 48 that are positioned intermediate 58 between the distal and proximal ends 54, 56. As a result, the stent 12 may be released without concentrating the pushing force on one part of the stent structure, such as the proximal end 56, as is common with conventional delivery systems. This may reduce the potential for buckling or deforming the stent structure during release due to large axial forces. Furthermore, because the axial pushing forces are more evenly distributed along the length of the stent 12, longer stents than commonly used may be used with the delivery system 10. This may be particularly beneficial in situations where a relatively long portion of an artery requires treatment by a stent. Traditionally, multiple stents have been implanted in these situations in order to treat the entire portion of the artery in need of treatment. Typically, this has been required because the relatively low column strength of conventional stents has limited the length of stents that may be used in conventional delivery systems. As a result, several separate introductions of different delivery systems are required to implant all of the stents that are needed. By contrast, a single, long stent could be used with the delivery system 10 to treat an entire portion of an artery needing a long length of treatment. This would reduce costs, shorten the time of the medical procedure, and reduce possible artery damage from multiple introductions.

Another advantage of the delivery system 10 is that multiple stents may be implanted with a single delivery system 10 and a single introduction. For example, two or more stents 12 may be loaded into the delivery system between the shaft 14 and the sheath 28, with the stents 12 being longitudinally adjacent or spaced apart along the length of the delivery system 10. With this arrangement, the first stent located closest to the distal end may be released first, and the next stent located next to the first stent may be released second. The number of stents 12 that could be loaded into the delivery system 10 depends on the overall length of the delivery system 10 and other factors that may be determined by physicians. One disadvantage of conventional delivery systems that makes it difficult to load more than one stent into the delivery system is that the shaft of the delivery system typically extends out from the distal end of the sheath after a stent is released. The length of the extended portion of the shaft is typically equal to the length of the released stent. Thus, if more than one stent is to be released, the shaft will successively extend further out from the sheath as each additional stent is released. This can make it impractical to release multiple stents since there may not be sufficient length available in the arterial lumen to accommodate the extended length of the shaft. In addition, the extended length of the shaft may cause damage to the wall of the artery or may damage nearby organs. By contrast, the described delivery system 10 may be used to withdraw the shaft 14 so that the distal ends 18, 32 of the shaft 14 and the sheath 28 remain in relative proximity to each other. For example, as described above, the stent 12 may be released by turning the shaft 14 so that the stent 12 is threaded out the distal end 18, 32 of the shaft 14 and the sheath 28. In this application, the relative longitudinal positions of the shaft 14 and the sheath 28 do not change significantly during release of the stent 12. Thus, after the stent 12 is released, the shaft 14 does not extend significantly from the distal end 32 of the sheath 28. In addition, as the first stent is being released, the next stent is being simultaneously threaded toward the distal end 18, 32 of the delivery system 10 for release after the first stent. Alternatively, the first stent may be released conventionally by withdrawing the sheath 28 rearward from the shaft 14 and the stent 12. After the first stent is released, the shaft 14 may then be turned in reverse to withdraw the shaft 14 back into the sheath 28. The next stent will then be located near the distal end 18, 32 of the delivery system 10 and may be released either conventionally or by rotation. Thus, the delivery system 10 may be used in several ways to implant multiple stents while minimizing the length of the shaft 14 that extends from the distal end 32 of the sheath 28.

While preferred embodiments of the invention have been described, it should be understood that the invention is not so limited, and modifications may be made without departing from the invention. For example, although the embodiment described above is adapted for intravascular delivery of a self-expandable stent, the structure taught herein may also be adapted for other uses, such as the delivery of single or multiple implantable valves or other endoprosthetic devices. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with all embodiments of the invention.

I claim:

1. A medical system comprising:
   an implantable medical device; and
   a delivery system comprising:
      a shaft comprising an outer circumference with a helical raised region and an interposed helical recessed region, said helical raised and recessed regions disposed along a distal portion of said shaft;
      a sheath comprising an inner circumference with a longitudinal raised region and an interposed longitudinal recessed region, said longitudinal raised and recessed regions disposed along a distal portion of said sheath;
      wherein said outer circumference of said shaft is adapted to be disposed within said inner circumference of said sheath, said helical raised region of said shaft having a smaller outer diameter than an inner diameter of said raised longitudinal region of said sheath, said shaft thereby being longitudinally moveable within said sheath without rotating either of said shaft or said sheath; and
      wherein said implantable medical device is receivable between said shaft and said sheath, said helical raised and recessed regions of said shaft engaging an inner surface of said implantable medical device and said longitudinal raised and recessed regions of said sheath engaging an outer surface of said implantable medical device;
      wherein relative rotational movement between said shaft and said sheath, without any relative axial movement between said shaft and said sheath, is capable of causing said implantable medical device to move longitudinally relative to said shaft over a distance at least an entire length of said implantable medical device with substantially no relative rotational movement between said implantable medical device and said sheath;
      wherein said implantable medical device may be released from a distal end of said delivery system.

2. The medical system according to claim 1, further comprising a first handle connected to said sheath and a second handle connected to a rod extending through said first handle, said rod being connected to said shaft.

3. The medical system according to claim 1, further comprising a first raised portion on said inner surface of said implantable medical device and a second raised portion on said outer surface of said implantable medical device, said first raised portion being engaged by said helical raised and recessed regions of said shaft, and said second raised portion being engaged by said longitudinal raised and recessed regions of said sheath.

4. The medical system according to claim 3, wherein said implantable medical device comprises radiopaque markers, said first raised portion and said second raised portion being formed by said radiopaque markers.

5. The medical system according to claim 1, wherein said implantable medical device is a self-expandable stent comprising a ring of undulating struts, said sheath compressing said stent into a collapsed diameter for intravascular delivery.

6. The medical system according to claim 5, further comprising first raised portions on said inner surface of said stent and second raised portions on said outer surface of said stent, said first raised portions being engaged by said helical raised and recessed regions of said shaft, and said second raised portions being engaged by said longitudinal raised and recessed regions of said sheath, said stent comprising at least one of said first raised portions and said second raised portions at each end of said stent.

7. The medical system according to claim 6, wherein said stent comprises radiopaque markers, said first raised portions and said second raised portions being formed by said radiopaque markers.

8. The medical system according to claim 6, wherein said stent further comprises at least one of said first raised portions and said second raised portions at an intermediate position between said ends of said stent.

9. The medical system according to claim 8, wherein said stent comprises radiopaque markers, said first raised portions and said second raised portions being formed by said radiopaque markers.

10. The medical system according to claim 1, wherein said helical raised and recessed regions of said shaft and said longitudinal raised and recessed regions of said sheath extend a length of at least two of said implantable medical devices, at least two of said implantable medical devices thereby being receivable between said shaft and said sheath one after the other.

11. The medical system according to claim 10, wherein said at least two implantable medical devices are self-expandable stents, said sheath compressing said stents into collapsed diameters for intravascular delivery.

12. The medical system according to claim 1, wherein said helical recessed region of said shaft comprises at least one groove.

13. The medical system according to claim 1, wherein said shaft further comprises a lumen extending through said shaft adapted to receive a guidewire.

14. The medical system according to claim 1, wherein said implantable medical device is a self-expandable stent, said sheath compressing said stent into a collapsed diameter for intravascular delivery; further comprising a first handle connected to said sheath and a second handle connected to a rod extending through said first handle, said rod being connected to said shaft; and said shaft further comprising a lumen extending through said shaft adapted to receive a guidewire.

15. The medical system according to claim 14, further comprising first raised portions on said inner surface of said stent and second raised portions on said outer surface of said stent, said first raised portions being engaged by said helical raised and recessed regions of said shaft, and said second raised portions being engaged by said longitudinal raised and recessed regions of said sheath, said stent comprising at least one of said first raised portions and said second raised portions at each end of said stent and at an intermediate position between said ends of said stent; wherein said stent comprises radiopaque markers said first raised portions and said second raised portions being formed by said radiopaque markers; said helical raised and recessed regions of said shaft and said longitudinal raised and recessed regions of said sheath extend a length of at least two of said implantable medical devices, at least two of said implantable medical devices thereby being receivable between said shaft and said sheath one after the other; and said helical recessed region of said shaft comprises at least one groove.

16. A medical system comprising:
an implantable medical device; and
a delivery system comprising:
a shaft comprising an outer circumference with a helical raised region and an interposed helical recessed region, said helical raised and recessed regions disposed along a distal portion of said shaft;
a sheath comprising an inner circumference disposed along a distal portion of said sheath; and
wherein said outer circumference of said shaft is adapted to be disposed within said inner circumference of said sheath, said implantable medical device thereby being receivable between said shaft and said sheath, said helical raised and recessed regions of said shaft engaging an inner surface of said implantable medical device, said implantable medical device comprising a portion on an outer surface of said implantable medical device engaging said sheath, said portion restricting relative rotational movement between said implantable medical device and said sheath, and wherein relative rotational movement between said shaft and said sheath, without any relative axial movement between said shaft and said sheath, is capable of causing said implantable medical device to move longitudinally relative to said shaft over a distance at least an entire length of said implantable medical device with substantially no relative rotational movement between said implantable medical device and said sheath;
wherein said implantable medical device may be released from a distal end of said delivery system.

17. The medical system according to claim 16, further comprising a first handle connected to said sheath and a second handle connected to a rod extending through said first handle, said rod being connected to said shaft.

18. The medical system according to claim 16, further comprising a raised portion on an inner surface of said implantable medical device, said raised portion being engaged by said helical raised and recessed regions of said shaft.

19. The medical system according to claim 18, wherein said implantable medical device comprises radiopaque markers, said raised portion and said portion on said outer surface of said implantable medical device being formed by said radiopaque markers.

20. The medical system according to claim 16, wherein said implantable medical device is a self-expandable stent comprising a ring of undulating struts, said sheath compressing said stent into a collapsed diameter for intravascular delivery.

21. The medical system according to claim 20, further comprising raised portions on said inner surface of said stent, said raised portions being engaged by said helical raised and recessed regions of said shaft, said stent comprising at least one of said raised portions and said portions on said outer surface of said stent at each end of said stent.

22. The medical system according to claim 21, wherein said stent comprises radiopaque markers, said raised portions and said portions on said outer surface of said stent being formed by said radiopaque markers.

23. The medical system according to claim 21, wherein said stent further comprises at least one of said raised portions and said portions on said outer surface of said stent at an intermediate position between said ends of said stent.

24. The medical system according to claim 23, wherein said stent comprises radiopaque markers, said raised portions and said portions on said outer surface of said stent being formed by said radiopaque markers.

25. The medical system according to claim 16, wherein said helical raised and recessed regions of said shaft extend a length of at least two of said implantable medical devices, at least two of said implantable medical devices thereby being receivable between said shaft and said sheath one after the other.

26. The medical system according to claim 25, wherein said at least two implantable medical devices are self-expandable stents, said sheath compressing said stents into collapsed diameters for intravascular delivery.

27. The medical system according to claim 16, wherein said helical recessed region of said shaft comprises at least one groove.

28. The medical system according to claim 16, wherein said shaft further comprises a lumen extending through said shaft adapted to receive a guidewire.

29. The medical system according to claim 16, wherein said implantable medical device is a self-expandable stent, said sheath compressing said stent into a collapsed diameter for intravascular delivery; further comprising a first handle connected to said sheath and a second handle connected to a rod extending through said first handle, said rod being connected to said shaft; and said shaft further comprising a lumen extending through said shaft adapted to receive a guidewire.

30. The medical system according to claim 29, further comprising raised portions on said inner surface of said stent, said raised portions being engaged by said helical raised and recessed regions of said shaft, said stent comprising at least one of said raised portions and said portions on said outer surface of said stent at each end of said stent and at an intermediate position between said ends of said stent; wherein said stent comprises radiopaque markers said raised portions and said portions on said outer surface of said stent being formed by said radiopaque markers; said helical raised and recessed regions of said shaft extend a length of at least two of said implantable medical devices, at least two of said medical devices thereby being receivable between said shaft and said sheath one after the other; and said helical recessed region of said shaft comprises at least one groove.

* * * * *

UNITED STATES PATENT AND TRADEMARK OFFICE
CERTIFICATE OF CORRECTION

PATENT NO. : 7,578,838 B2  Page 1 of 1
APPLICATION NO. : 11/034913
DATED : August 25, 2009
INVENTOR(S) : Jeffry S. Melsheimer It is certified that error appears in the above-identified patent and that said Letters Patent is hereby corrected as shown below:

In the Claims

In column 12, claim 30, line 57, immediately after "radiopaque markers" insert --,--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,578,838 B2 |
| APPLICATION NO. | : 11/034913 |
| DATED | : August 25, 2009 |
| INVENTOR(S) | : Jeffry S. Melsheimer |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 653 days.

Signed and Sealed this

Seventh Day of September, 2010

David J. Kappos
*Director of the United States Patent and Trademark Office*